United States Patent [19]

Gold et al.

[11] Patent Number: 4,831,157

[45] Date of Patent: May 16, 1989

[54] PREPARATION OF ANGIOTENSIN-CONVERTING ENZYME INHIBITORS

[75] Inventors: Elijah H. Gold; Bernard R. Neustadt, both of West Orange; Elizabeth M. Smith, Verona, all of N.J.

[73] Assignee: Schering Corporation, Kenilworth, N.J.

[21] Appl. No.: 250,300

[22] Filed: Sep. 28, 1988

Related U.S. Application Data

[60] Division of Ser. No. 817,639, Jan. 10, 1986, abandoned, which is a continuation-in-part of Ser. No. 635,390, Jul. 30, 1984, Pat. No. 4,587,258, which is a continuation-in-part of Ser. No. 258,484, Apr. 28, 1981, abandoned, which is a continuation-in-part of Ser. No. 201,649, Oct. 28, 1980, abandoned, which is a continuation-in-part of Ser. No. 199,886, Oct. 23, 1980, abandoned.

[30] Foreign Application Priority Data

Oct. 15, 1981 [EP] European Pat. Off. ........ 81108348.4
Jul. 26, 1985 [WO] PCT Int'l Appl. ... PCT/US85/01406

[51] Int. Cl.$^4$ .......................................... C07D 487/04
[52] U.S. Cl. .................................................. 548/452
[58] Field of Search ......................................... 548/452

[56] References Cited

U.S. PATENT DOCUMENTS

4,727,160 2/1988 Teetz et al. .................. 548/452

FOREIGN PATENT DOCUMENTS

50800 10/1981 European Pat. Off. .
79022 11/1982 European Pat. Off. .
0084164 7/1983 European Pat. Off. ............ 548/452
2525604 10/1983 France ................................ 548/483

OTHER PUBLICATIONS

R. Bonnet et al, *J. Chem. Soc.*, 2087 (1959).
M. Mitzlaff et al, *Liebigs Ann. Chem.*, 1713 (1978).
V. Asher et al., *Tetrahedron Lett.*, 141 (1981).
G. B. R. deGraaf et al., *Rec. Trav. Chem.*, 81,786 (1962).
K. Kariyone, *Chem. Pharm. Bull.*, 8, 1110 (1960).
K. Kariyone, *Chem. Abstr.*, 53, 21940 (1959).
D. Sieback and D. Enders, *Angew. Chem. Internat.*, Edit 14,15 (1975).
A. G. Anderson et al., *J. Org. Chem.*, 43,55 (1978).
H. Booth et al., *J. Chem. Soc.*, 1050 (1959).
F. E. King et al., *J. Chem. Soc.*, 250 (1953).
E. D. Bergman et al., *J. Amer. Chem. Soc.*, 78,1482 (1956).
H. T. Nagasawa et al., *J. Med. Chem.*, 14,501 (1971).
J. A. Elberling et al., *J. Heterocycl. Chem.*, 9,411 (1971).
R. Henning et al., *Tetrahedron Lett.*, 24, 5339 (1984).
S. V. Kessar et al, *J. Indian Chem. Soc.*, 40, 655 (1963).
W. C. Francis et al., *J. Amer. Chem. Soc.*, 80, 6238 (1958).
R. J. Wineman et al., *J. Amer. Chem. Soc.*, 80, 6233 (1958).
E. D. Bergman et al., *J. Amer. Chem. Soc.*, 80, 3135 (1958).

*Primary Examiner*—David B. Springer
*Attorney, Agent, or Firm*—Anita W. Magatti; Stephen I. Miller; Gerald S. Rosen

[57] ABSTRACT

Novel compounds with angiotensin-converting enzyme inhibitory activity are disclosed. Such compounds are useful in the treatment of cardiovascular disorders, especially hypertension and congestive heart failure, and are useful in the treatment of glaucoma. Also disclosed is a novel process for preparing intermediates useful in the preparation of the claimed compounds.

1 Claim, No Drawings

4,831,157

PREPARATION OF ANGIOTENSIN-CONVERTING ENZYME INHIBITORS

RELATED APPLICATIONS

This application is a division of application Ser. No. 817,639, filed Jan. 10, 1986, now abandoned, which is a continuation-in-part of U.S. Ser. No. 635,390, now U.S. Pat. No. 4,587,258, filed July 30, 1984, which is a continuation-in-part of U.S. Ser. No. 258,484, now abandoned, filed Apr. 28, 1981, which is a continuation-in-part of U.S. Ser. No. 201,649, filed Oct. 28, 1980, now abandoned, which is a continuation-in-part of U.S. Ser. No. 199,886, filed Oct. 23, 1980, now abandoned.

SUMMARY OF THE INVENTION

The invention relates to compounds which are inhibitors of angiotensin-converting enzyme and useful in the treatment of cardiovascular disorders especially as antihypertensive agents and also in the treatment of congestive heart failure and of glaucoma. The compounds of this invention are represented by the formula

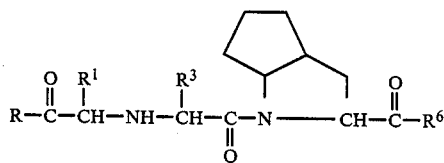

I and the pharmaceutically acceptable salts thereof, wherein R and $R^6$ are the same or different and are hydroxy, lower alkoxy, lower alkenoxy, diloweralkylamino lower alkoxy (e.g. dimethylaminoethoxy), acylamino lower alkoxy (e.g. acetylaminoethoxy), acyloxy lower alkoxy (e.g. pivaloyloxyethoxy), aryloxy (e.g. phenoxy), arylloweralkoxy (e.g. benzyloxy), amino, lower alkylamino, diloweralkylamino, hydroxyamino, aryllower alkylamino (e.g. benzylamino), or substituted aryloxy or substituted arylloweralkoxy wherein the substituent is methyl, halo or methoxy;

$R^1$ is hydrogen, alkyl of from 1 to 10 carbon atoms, including branched and cyclic and unsaturated (e.g. allyl) alkyl groups, substituted lower alkyl wherein the substituent is hydroxy, lower alkoxy, aryloxy (e.g. phenoxy), substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio (e.g. phenylthio), substituted arylthio, carboxy, carbamoyl, lower alkoxycarbonyl, aryl (e.g. phenyl or naphthyl), substituted aryl, aralkyloxy, substituted aralkyloxy, aralkylthio, or substituted aralkylthio, wherein the aryl or heteroaryl portion of said substituted aryloxy, heteroaryloxy, arylamino, arylthio, aryl, aralkyloxy or aralkylthio groups is substituted with a group selected from halo, loweralkyl, hydroxy, lower alkoxy, amino, aminomethyl, carboxyl, cyano and sulfamoyl; and $R^3$ is hydrogen, lower alkyl, phenyl lower alkyl, aminomethylphenyl lower alkyl, hydroxyphenyl lower alkyl, hydroxy lower alkyl, acylamino lower alkyl (e.g. benzoylamino lower alkyl or acetylamino lower alkyl), amino lower alkyl, dimethylamino lower alkyl, guanidino lower alkyl, imidazolyl lower alkyl, indolyl lower alkyl, or lower alkylthio lower alkyl.

As used herein, acyl includes

wherein $R^{12}$ is lower alkyl, lower alkenyl or aryl. The lower alkyl or lower alkenyl groups except where noted otherwise are represented by any of the variables including straight and branched chain hydrocarbon radicals from one to six carbon atoms, for example, methyl, ethyl, propyl, isopropyl, butyl, isobutyl, t-butyl, pentyl, isopentyl, hexyl or vinyl, allyl, butenyl and the like. Cycloalkyl groups include bridged and nonbridged groups. The aralkyl groups represented by any of the above variables have from one to four carbon atoms in the alkyl portion thereof and include for example, benzyl, p-methoxybenzyl and the like. Halo means chloro, bromo, iodo or fluoro. Aryl, where it appears in any of the radicals, except where noted, represents phenyl or naphthyl. Heteroaryl groups where they appear include for example pyridyl, thienyl, furyl, indolyl, benzothienyl, imidazolyl and thiazolyl. The $R^1$ and $R^3$ substituted lower alkyl moieties are exemplified by groups such as

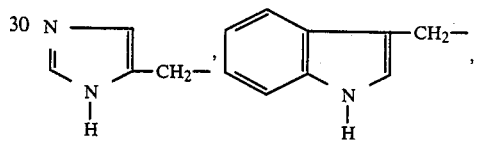

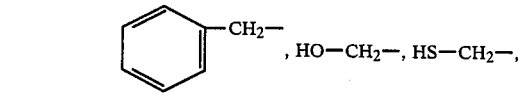

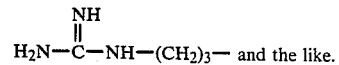 and the like.

Preferred compounds of formula I are those in which R is hydroxy and lower alkoxy, $R^1$ is lower alkyl and substituted lower alkyl wherein the substituent is aryl, $R^3$ is lower alkyl and aminoloweralkyl and $R^6$ is hydroxy.

The aforementioned compounds of the formula I, as defined above, include all possible stereoisomers. Preferred stereoisomers are the cis,endo-octahydrocyclopenta[b]pyrrole-2(S)-carboxylic acids. Particularly preferred compounds are 1-[N-(1(S)-carboxy-3-phenylpropyl)-(S)-alanyl]-cis,endo-octahydrocyclopenta[b]pyrrole-2(S)-carboxylic acid, 1-[N-(1(S)-carboethoxy-3-phenylpropyl)-(S)-alanyl]-cis,endo-octahydrocyclopenta[b]pyrrole-2(S)-carboxylic acid 1-[Nα-(1(S)-carboethoxy-3-phenylpropyl)-(S)-lysyl]-cis,endo-octahydrocyclopenta[b]pyrrole-2(S)-carboxylic acid, 1-[Nα-(1(S)-carboxy-3-phenylpropyl)-(S)-lysyl]-cis,endo-octahydrocyclopenta[b]pyrrole-2(S)-carboxylic acid, 1-[N-(1(S)-carboxybutyl)-(S)-alanyl]-cis,endo-octahydrocyclopenta[b]pyrrole-2(S)-carboxylic acid, 1-[N-(1(S)-carboethoxybutyl)-(S)-alanyl]-cis,endo-octahydrocyclopenta[b]pyrrole-2(S)-carboxylic acid, 1-[Nα-(1(S)-carboethoxybutyl)-(S)-lysyl]-cis,endo-octahydrocyclopenta[b]pyrrole-2(S)-carboxylic acid, and 1-[Nα-(1(S)-carboxybutyl)-(S)-lysyl]-cis,endo-octahydrocyclopenta[b]pyrrole-2(S)-carboxylic acid or their hydrochloride salts. A most preferred compound is 1-[N-(1(S)-carboethoxy-3-phenylpropyl)-(S)-alanyl]-cis,endo-octahydrocyclopenta[b]pyrrole-2-(S)-carboxylic acid and its hydrochloride salt.

The compounds of the present invention can be produced by methods known in the art using appropriate analogous reactants.

One of ordinary skill in the art will appreciate that not all of the compounds of this invention may be readily prepared by any one process, but by selecting the appropriate process from those disclosed below, the skilled artisan may prepare all the compounds of this invention.

The starting materials which are required for the processes herein described are known in the literature or can be made by known methods from known compounds.

For example, the intermediate octahydrocyclopenta[b]pyrrole-2-carboxylate, III,

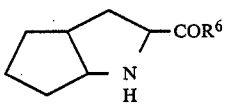

III wherein $R^6$ is as defined above, may be prepared by more than one method, including methods analogous to those known in the art, from starting materials described in the literature.

Compounds of formula III consist of eight stereoisomers composed of four racemic pairs; the two cis epimers, IIIa and IIIb, and the two trans epimers, IIIc and IIId.

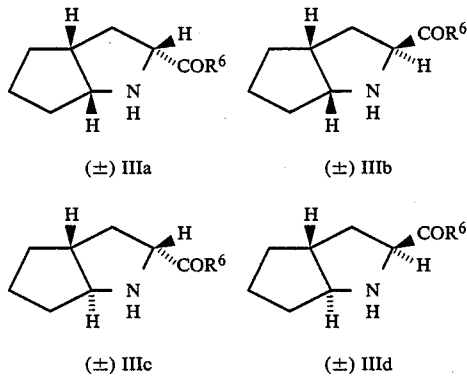

If desired, each racemic pair may be separated into its component enantiomers by resolution methods well described in the art.

A novel process for the synthesis of IIIa involves catalytic reduction of 1-benzyl-1,4,5,6-tetrahydrocyclopenta[b]pyrrole-2-carboxylate, a compound of formula II wherein $R^6$ is as defined above, which is prepared by reacting imine IV with a halo pyruvate ester such as ethyl bromopyruvate, as exemplified in the following process:

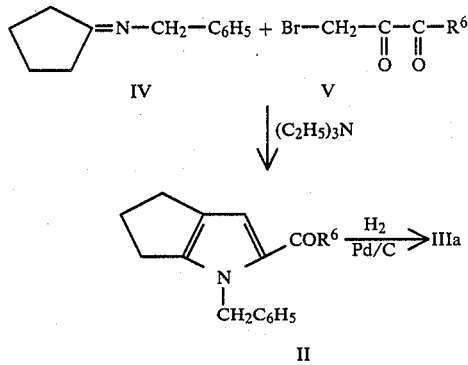

The above process preferably uses a lower alkyl ester of bromo pyruvate (e.g. $R^6$ is ethoxy, methoxy or t-butoxy). Preferably, equimolar amounts of reactants are used. The reaction is carried out in an inert solvent such as an alcohol (e.g. ethanol), acetonitrile or dimethylformamide in the presence of a base such as triethylamine. The reaction may be carried out at from 0°–100° C. for 2–8 hours, but is preferably carried out at low temperatures (e.g. 0°–5° C.) for approximately 2 hours, then at reflux (temperature depends on solvent) for 2 hours. Catalytic reduction of the resultant 1-benzyl-1,4,5,6-tetrahydrocyclopenta[b]pyrrole-2-carboxylate to saturate the ring and remove the benzyl group is carried out in a solvent such as an alcohol (e.g. ethanol) in the presence of hydrogen gas and a catalyst such as $Pd(OH)_2$ on carbon or other appropriate catalysts. The resultant product may be isolated by methods well known to those skilled in the art, e.g. by treating with an acid such as HCl to prepare the salt, followed by removal of the salt (e.g. by basifying with sodium hydroxide) to obtain the compound of formula IIIa.

Additional methods for synthesizing compounds of formula III will be described below.

By utilizing intermediate III, the compounds of the present invention can be produced by various methods and subroutes, some of which are depicted in the following equations. Additional methods may be found in European Patent Application No. 50,800, published May 5, 1982. Reactive groups not involved in the condensation described below such as amino, carboxy, mercapto, etc., may be protected by methods standard in peptide chemistry prior to the coupling reactions and subsequently deprotected to obtain the desired products. Such reactions are demonstrated in the Examples.

Compounds of the present invention may be prepared as follows:

The intermediate III is coupled by known methods with a suitably N-protected alpha amino acid of formula VI wherein Pr is a protecting group, and the product is then deprotected by conventional means to produce the compound VII

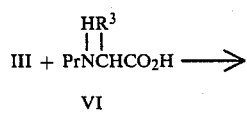

-continued

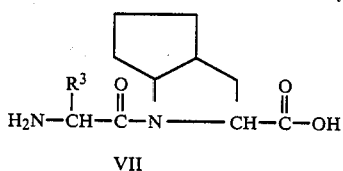
VII wherein $R^3$ is as defined hereinabove.

Dipeptide VII is then condensed with keto acid (or ester) VIII in aqueous solution, optimally near neutrality or in a suitable organic solvent (for example, $CH_3OH$) in the presence of sodium cyanoborohydride to give I.

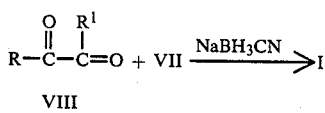
VIII

Alternatively, the intermediate Schiff base, enamine or aminol may be catalytically reduced to yield product I, for example, by hydrogen in the presence of 10% palladium on carbon or in the presence of Raney Nickel. The ratio of diastereomeric products formed may be altered by choice of catalyst.

If R is a carboxy protecting group such as alkoxy or benzyloxy, it can be converted by well known methods such as hydrolysis or hydrogenation to I, wherein R is hydroxy. This is also the case in all of the methods referred to below.

Alternatively VIII can be condensed with an amino acid VIa under the same conditions to yield amino acid IX.

$$\underset{\text{VIa}}{\overset{R^3}{\underset{|}{H_2NCH-COOH}}} + VIII \xrightarrow{NaBH_3CN}$$

$$\underset{\text{IX}}{\overset{O\ R^1\ R^3}{\underset{||\ |\ |}{R-C-CHNHCHCOOH}}}$$

The carboxylic acid function in VIa may be protected by removable ester groups such as benzyl, ethyl, t-butyl, and the like. Subsequent coupling of IX by known methods with amino acid derivative III gives I.

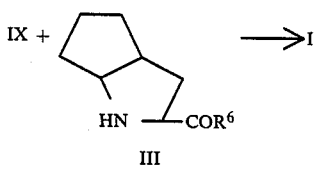
III

The known methods encompass reactive group protection during the coupling reactions, for example, amino groups in compounds VI and in substituents $R^1$ and/or $R^3$ may be protected by N-formyl, N-t-butoxycarbonyl and N-carbobenzyloxy groups followed by their removal to yield I and/or VII. Furthermore, the carboxylic acid function in III may be protected by removable ester groups such as benzyl, ethyl, t-butyl, and the like. As desired, protecting groups may be removed by known methods. Coupling agents in these synthetic routes are typically those useful in peptide chemistry such as dicyclohexylcarbodiimide (DCC) or diphenylphosphoryl azide (DPPA), and VI and/or IX may be activated via the intermediacy of active esters such as those derived from 1-hydroxy-benzotriazole or N-hydroxysuccinimide.

The following additional non-exhaustive series of processes for preparing the cis,endo (IIIa) and cis,exo (IIIb) isomers of III, will exemplify some of the known methodology that may be employed by those of ordinary skill in the art in preparing intermediates of formula III.

Analogy Process 1

Conventional oxidation, using for example mercuric acetate, [e.g., see R. Bonnet, et al, *J. Chem. Soc.*, 2087 (1959)] of the known cis-octahydrocyclopenta[b]pyrrole, X, wherein $R^7$ is hydrogen, to imine XI, followed by addition of HCN to XI, affords the cis,endo and cis,exo nitriles, XIIa and XIIb. Nitriles XIIa and XIIb may be hydrolyzed under standard acidic or basic conditions to IIIa and IIIb, wherein $R^6$ is OH. The reaction scheme is as follows:

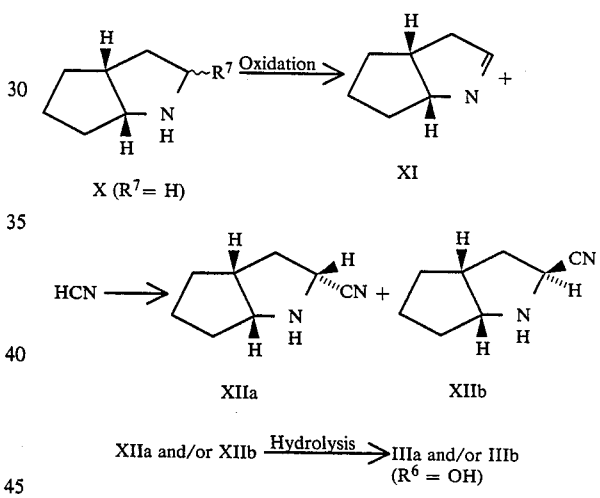

XIIa and/or XIIb $\xrightarrow{\text{Hydrolysis}}$ IIIa and/or IIIb
($R^6$ = OH)

Analogy Process 2

IIIa and IIIb may be obtained by the known electrolytic oxidation of acylated amines such as XIII [M. Mitzlaff et al, *Liebigs Ann. Chem.* 1713 (1978)], in the presence of an alcohol such as methanol, to ethers XIVa and XIVb, followed by conventional replacement of the ether group by HCN to afford compounds XVa and XVb. Alternatively XVa and XVb may be obtained by treatment of XIV with trimethylsilylcyanide in the presence of boron trifluoride etherate [V. Asher et al., *Tetrahedron Lett.*, 141 (1981)]. Typical acyl groups are acetyl, trifluoroacetyl, benzoyl and the like. Compounds XVa and XVb may then be hydrolyzed by standard means to compounds IIIa and IIIb, or compounds XVa and XVb may first be partially hydrolyzed to XIIa and XIIb, a reaction which is known to be especially facile when the acyl group is trifluoroacetyl and the hydrolyzing agent is methanolic potassium carbonate. Compounds XIII are available by conventional acylation of compound X.

The reaction schemes are as follows:

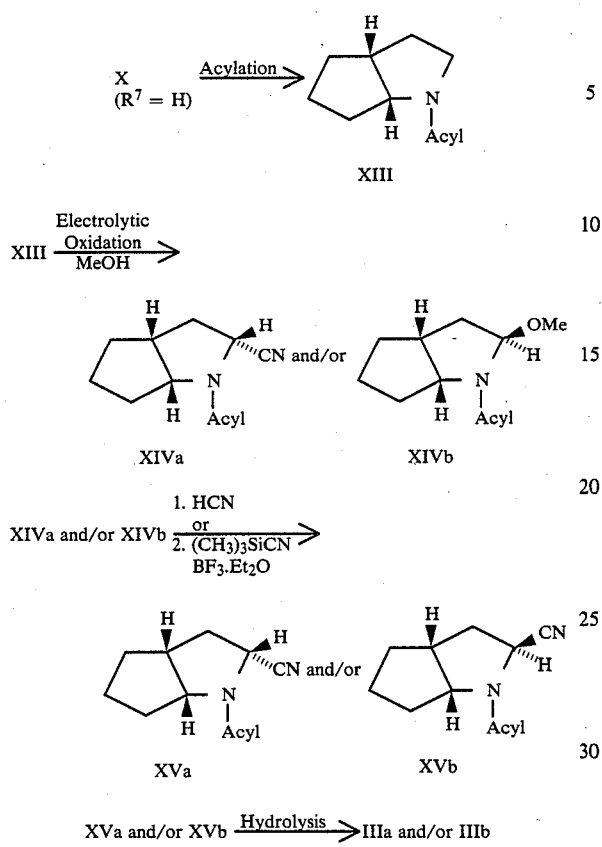

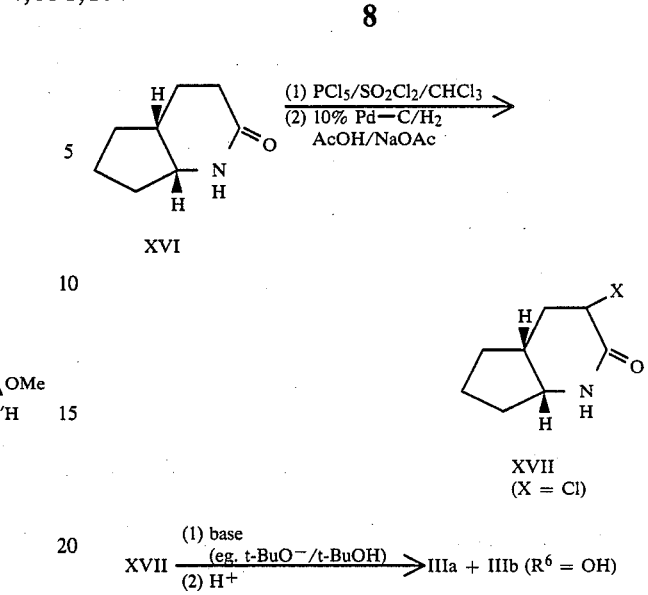

Compounds IIIa and IIIb, wherein $R^6$ is OH, are readily esterified by standard methods to afford the corresponding esters as defined for $R^6$ above. Alternatively, many of the esters corresponding to IIIa and IIIb may be prepared by direct solvolysis of the nitriles XIIa and/or XIIb. Thus, for example, the ethyl esters corresponding to IIIa and/or IIIb (i.e., $R^6=OCH_2CH_3$) may be directly obtained by reaction of XIIa and/or XIIb in ethanol, for example in the presence of an acid such as HCl. Conversely, the esters corresponding to IIIa and IIIb are convertible to their corresponding acids (i.e., wherein $R^6$ is OH) by conventional hydrolytic methods.

Analogy Process 3

IIIa and IIIb can be obtained by the well-known Favorskii-type ring contraction of α-halo lactams, XVII, under a variety of basic conditions [see for example, G. B. R. deGraaf, et al., *Rec. Trav. Chem.*, 81, 786 (1962); K. Kariyone, *Chem. Pharm. Bull.*, 8, 1110 (1960); *Chem. Abstr.*, 53, 21940 (1959); H. T. Nagasawa et al., *J. Med. Chem.*, 14, 501 (1971); J. A. Elberling et al., *J. Heterocycl. Chem.*, 9, 411 (1972); R. Henning et al., *Tetrahedron Lett.*, 24, 5339 (1984)]. The α-halo lactams XVII, wherein X is chloro or bromo, may be prepared from the known lactam XVI [S. V. Kessar et al., *J. Indian Chem. Soc.*, 40, 655 (1963)] by the process descrbbed by W. C. Francis et al [*J. Amer. Chem. Soc.*, 80, 6238 (1958)] and R. J. Wineman et al. [Ibid., 80, 6233 (1958)]. An example of the overall process, wherein X is chloro, is as follows:

Analogy Process 4

Compounds IIIa and IIIb can be prepared from compound X, wherein $R^7$ is hydrogen, by known methods of electrophilic substitution alpha to activated amines [for a review, see D. Sieback and D. Enders, *Angew. Chem. Internat. Edit.*, 14, 15 (1975)]. Thus, for example, N-nitrosation of compound X, wherein $R^7$ is hydrogen, with a reagent such as ethyl nitrite or the like affords the N-nitroso derivative XXIII. Treatment of compound XXIII with a strong base such as, for example, the lithium salt of diisopropylamine to remove the alpha hydrogen (intermediate XXIV), followed by carboxylation with carbon dioxide and subsequent removal of the N-nitroso group by known methods, such as with HBr in glacial acetic acid, affords compound IIIa and IIIb, wherein $R^6$ is hydrogen.

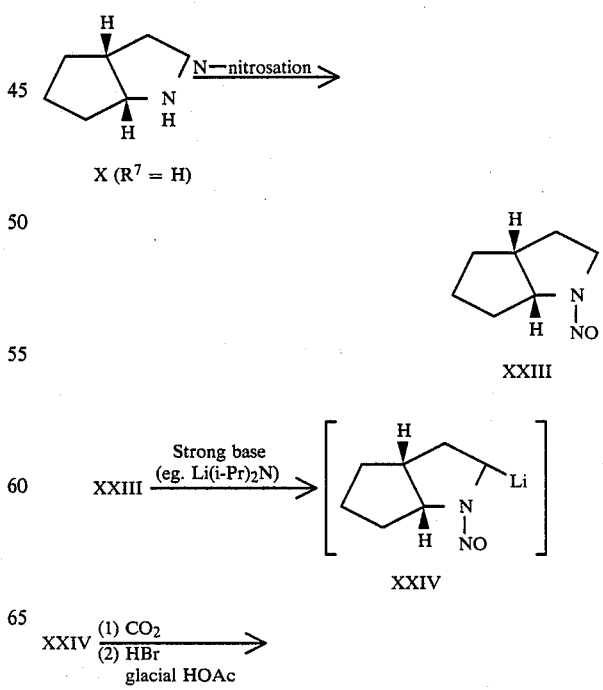

9

-continued

IIIa (R⁶ = H)    IIIb (R⁶ = H)

Analogy Process 5

Compounds of formula IIIa or IIIb may be prepared using any of several known processes for the preparation of compounds X wherein $R^7$ is hydrogen, among which are those described in: (1) A. G. Anderson et al, *J. Org. Chem.*, 43, 55 (1978); (2) M. G. Avetyan et al., U.S.S.R. Pat. No. 761,462, Sept. 7, 1980; (3) H. Booth et al, *J. Chem. Soc.*, 1050 (1959) and (4) F. E. King et al, Ibid., 250 (1953). Processes described in references (1) and (2) are essentially equivalent and involve as the first step the alkylation of cyclopentanone to intermediates of formula XX. Cyclopentanone is alkylated either as the free ketone of formula XVIII or as an enamine derivative of formula XXI, wherein Z is N-pyrrolidino or N-morpholino. The aforementioned pyrrolidine and morpholine groups exemplify the general enamine class of ketone "equivalents" [for a general reference, see (5) J. Smuzkowicz, "Advances in Organic Chemistry Methods and Results", Interscience, New York, N.Y. 1963, Vol. 4, Chapter 1]. Another general class of ketone "equivalents" are the enol ethers, represented by formula XXI, wherein Z is, for example, trimethylsilyloxy [i.e. $Z=OSi(CH_3)_3$]. Such alkylations of cyclopentanone have been carried out with a variety of haloalkyl compounds of formula XIX, among which are compounds wherein Q is aminoalkyl [reference (2)], cyanoalkyl [reference (1)] and carboxyalkyl [(6) E. D. Bergman et al, *J. Amer. Chem. Soc.*, 78, 1482 (1956); (7) E. D. Bergman et al, Ibid, 80, 3135 (1958)]. These alkylations of cyclopentanone may be represented as follows:

10

XXa is not isolated in either of the processes described in references (1) and (2).

Step 2 - (Ref. (1))

XXb → XXa ($R^7$ = H)

The third and fourth steps in the process from reference (1) involve the ring closure of intermediate XXa to the pyrroline(s) XXIIa, wherein $R^7$ is hydrogen (without isolation) (Step 3), and its concommitant reduction to afford compound X, wherein $R^7$ is hydrogen (Step 4). Similarly, the second and third steps in the process from reference (2) involve the ring closure of intermediate XXa to the pyrroline(s) XXIIa, wherein $R^7$ is hydrogen (with isolation) (Step 2), followed by reduction of XXIIa with sodium in methanol to yield compound X, wherein $R^7$ is hydrogen (Step 3).

Step 3 (Ref. (1)) = Step 2 (Ref. (2))

[XXa] ($R^7$ = H)

XXIIa ($R^7$ = H)
(not isolated in ref. (1))

Step 4 (Ref. (1)) = Step 3 (Ref. (2))

XXIIa ($R^7$ = H) — Reduction → X ($R^7$ = H)

Furthermore, one skilled in the art will recognize that using processes analogous to those exemplified by references (1), (2), (5), (6) and (7), compounds of formula III may be prepared by the alkylation of cyclopentanone

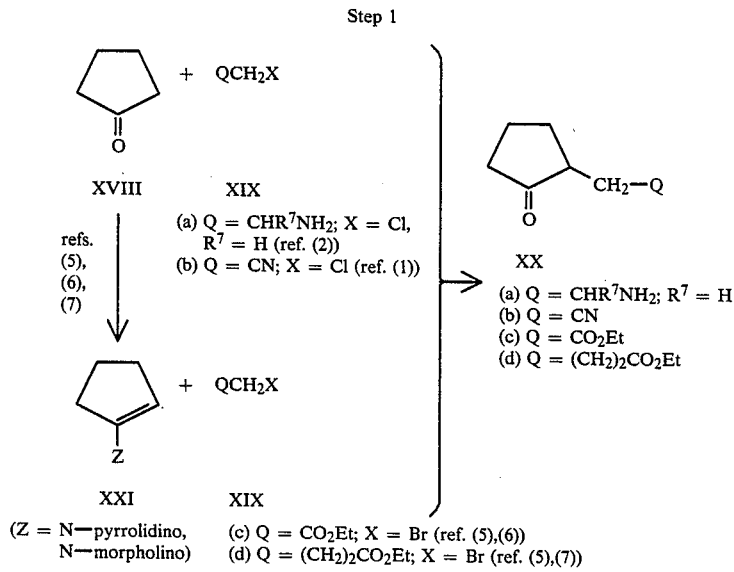

Step 1

XVIII + XIX refs. (5), (6), (7)

(a) Q = CHR⁷NH₂; X = Cl, R⁷ = H (ref. (2))
(b) Q = CN; X = Cl (ref. (1))

XX
(a) Q = CHR⁷NH₂; R⁷ = H
(b) Q = CN
(c) Q = CO₂Et
(d) Q = (CH₂)₂CO₂Et

XXI + XIX
(Z = N—pyrrolidino, N—morpholino)

(c) Q = CO₂Et; X = Br (ref. (5),(6))
(d) Q = (CH₂)₂CO₂Et; X = Br (ref. (5),(7))

The second step in the process from reference (1) is the reduction, by hydrogenation, of the nitrile intermediate XXb to the corresponding amine XXa. Amine (XVIII) or preferably by a cyclopentanone equivalent of formula XXI, wherein Z is, for example, the N-pyrrolidino, N-morpholino or trimethylsilyl enol ether group, with compounds of formula XIX, wherein Q is $CHR^7NHR^8$, and wherein $R^7$ is $COR^6$. The skilled artisan will appreciate that in the presence of a reactive carboxyl group, $COR^6$, it is desirable to protect the basic amino group in compounds XIX during the alkylation (step 1). Such protection is obviously achieved by acylation, for example, to yield compounds XIX wherein $R^8$ is acyl. A specific example is XIXe, wherein $R^7$ is $CO_2CH_3$ and $R^8$ is acetyl. The alkylation of cyclopentanone via its reactive equivalent of formula XXI with compounds XIXe to afford intermediate XXe, wherein Q is $CHR^7NHR^8$ and wherein $R^7$ is $CO_2CH_3$ and $R^8$ is acetyl may be exemplified as follows:

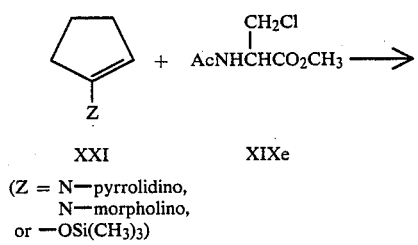

XXI      XIXe (Z = N—pyrrolidino,
N—morpholino,
or —OSi(CH_3)_3)

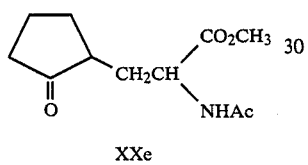

XXe

The Z function may be removed in a "one pot" process as is exemplified for the enamines in the referenced examples. Thus, the enamines are readily hydrolyzed under mild acid conditions to yield compound XXe. If the Z function is a silyl enol ether, e.g. compounds wherein Z is $-OSi(CH_3)_3$, the alkylation of XXI with XIXe may be carried out in the presence of fluoride ion or Lewis acid catalysts such as $TiCl_4$, $ZnBr_2$, $TiCl_2(i-PrO)_2$ and the like, to generate compound XXe.

As in the above described processes in references (1) and (2), intermediate XXe must be cyclized in step 2 to the pyrroline XXIIb, wherein $R^7$ is $COR^6$. Since the intermediate XXe in this example is N-protected by an acyl group, one skilled in the art will recognize that removal of the N-acyl protecting group may be readily accomplished by acid solvolysis, generally at elevated temperatures, which will concomitantly effect the previously exemplified cyclization reaction (i.e., XX→XXIIa) to afford compounds XXIIb. Compounds XXIIb are obtained as acids (i.e. wherein $R^7$ is $CO_2H$) when aqueous conditions are used, or as esters, (i.e. wherein $R^7$ is $COR^6$, and $R^6$ is as defined above, but not OH) when the solvolysis is carried out in an alcoholic solvent. The following reaction scheme exemplifies this process:

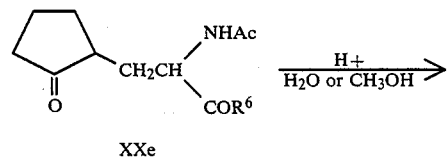

XXe

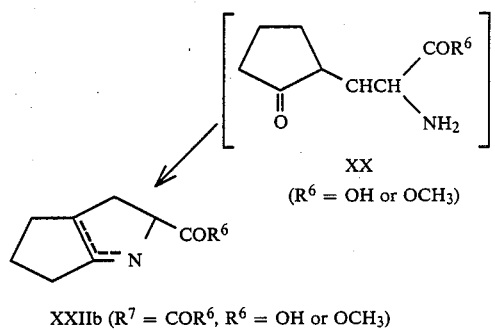

XXIIb ($R^7$ = $COR^6$, $R^6$ = OH or $OCH_3$)

The methods described in the processes utilized in references (1) and (2) for the reduction of XXIIa represent only two of several methods for performing this reaction known to those skilled in the art. Thus, for example, to obtain cis-X, wherein $R^7$ is $COR^6$, (i.e. IIIa and/or IIIb) from XXIIb, it is obvious that catalytic hydrogenation procedures represent a preferred method, and such a procedure is exemplified as follows, utilizing a palladium on carbon catalyst:

XXIIb           IIIa/IIIb ($R^6$ = OH)
                  = X ($R^7$ = $CO_2H$)

Additional well known reduction methods include the use of $NaBH_4$, $NaBH_3CN$ and the like.

A specific use of the analogy process described above is exemplified in European Patent Application No. 0079022 (1982) and German Patent Application Nos. 3226768 (1982) and 3143946 (1981).

Analogy Process 6

Those skilled in the art will appreciate that Compounds IIIa and IIIb are interconvertible, as are IIIc and IIId, by simple base catalyzed epimerization. Consequently, a synthesis of IIIa constitutes a synthesis of IIIb (and vice versa) and a synthesis of IIIc constitutes a synthesis of IIId (and vice versa). Such epimerizations are most conveniently carried out on the free base ester forms of these compounds in the absence or presence of additional basic catalysts such as potassium t-butoxide, triethylamine and the like. For example, IIIa                    IIIb In the compounds of the formula I, the carbon atoms to which $R^1$, $R^3$ and $COR^6$ are attached may be asymmetric. The compounds accordingly exist in diastereoisomeric forms or in mixtures thereof. The syntheses for making the compounds can utilize racemates, individual enantiomers or individual diastereomers as starting materials. Enantiomerically pure intermediates may be obtained by resolution methods known in 'the art. When diastereomeric products result from the synthetic procedures, the diastereomeric products can be separated by conventional chromatographic or fractional crystallization methods.

In general, the starred chiral centers in the amino acid part-structures, i.e.,

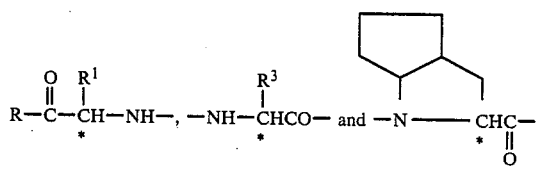

of Formula I are preferred in the configuration most similar to that of natural L-amino acids. Usually, natural L-amino acids are assigned the S-configuration. A notable exception is the natural amino acid L-cysteine which is assigned the R-configuration.

The compounds of this invention form salts with various inorganic and organic acids and bases which are also within the scope of the invention. Such salts include ammonium salts, alkali metal salts such as sodium and potassium salts (which are preferred), alkaline earth metal salts such as the calcium and magnesium salts, salts with organic bases e.g., dicyclohexylamine or N-methyl-D-glucamine, salts with amino acids such as arginine, lysine and the like. Also, salts with organic and inorganic acids may be prepared, e.g., HCl, HBr, $H_2SO_4$, $H_3PO_4$, methanesulfonic acid, toluenesulfonic acid, maleic acid, fumaric acid and camphorsulfonic acid. The non-toxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The following examples illustrate the preparation of the compounds of the present invention. The diasterioisomers prepared as set forth below may be isolated by column chromatography or by fractional crystallization.

EXAMPLE 1

Preparation of Ethyl Cis Octahydrocyclopenta[b]-Pyrrole-2-Carboxylate

A. General Procedure

Heat under reflux cis-octahydrocyclopenta[b]pyrrole [prepared by the methods of A. Bertho, et al, Chem. Ber. 92, 2218 (1959), wherein 2-oxo-cyclopentyl acetic acid is cyclized by reduction with Raney Nickel/$H_2$ in the presence of ammonia to obtain 2-keto-octahydrocyclopenta[b]pyrrole, which is then reduced with lithium aluminum hydride in etheral solution to yield cis-octahydrocyclopenta[b]pyrrole, or by the method of A. G. Anderson, Jr., et al, J. Org. Chem. 43, 55 (1978), discussed above] and mercuric acetate in water or up to 10% aqueous acetic acid for twenty hours or more, to obtain cis-3,3a,4,5,6,6a-hexahydrocyclopenta[b]pyrrole. Dissolve this compound in water and treat with potassium cyanide followed by 2N hydrochloric acid at 0° C. for two hours and at room temperature for approximately twenty hours to obtain 2-cyano-cis-octahydrocyclopenta[b]pyrrole. Heat this resultant compound in 6N hydrochloric acid under reflux for 6 hours followed by concentration of the reaction mixture to obtain cis-octahydrocyclopenta[b]pyrrole-2-carboxylic acid. If desired, adsorb the residue on an XAD-2 resin column and elute with methanol. Esterify by reaction with ethanol to obtain ethyl cis-octahydrocyclopenta[b]pyrrole-2-carboxylate, as a mixture of two epimers.

B. Detailed Procedures

1. Cis-3,3a,4,5,6,6a-Hexahydrocyclopenta[b]pyrrole

Method I

Heat under reflux 300 g (27 mmol) of cis-octahydrocyclopenta[b]-pyrrole (obtained from the recrystalized 3,5-dinitrobenzoate salt [See H. Booth et al, J. Chem. Soc., 1050 (1959)] by basification with sodium hydroxide to pH 11, extraction with ether and removal of the ether in vacuo) and 35 g (110 mmol) of mercuric acetate in 50 ml of 6% aquous acetic acid for six days. Cool the reaction mixture to ambient temperature, basify with NaOH to pH 11, filter and extract the solids with ether continuously for six days in a soxhlet apparatus. Combine the ethereal extract with the basic aqueous filtrate from the original filtration and extract continuously with ether for two days. Dry the ether layer over $K_2CO_3$, filter through a sintered glass funnel, and remove the ether in vacuo to obtain approximately 1.03 g of the crude title compound of Part 1 as a light amber oil. Gas liquid chromatography ($R_t$ 2.29 min. (instrument: Varian Vista Series 6000; 3% OV-1 on 80 Supelcoport; column dimensions 6'×2 mm I.D.; column temp. 110° C.; He flow rate, ca 20 ml/min). Mass spectrum (GLC/MS): 109 ($M^+$, 20%), 108 (15%), 82 (57% M-HCN), 81 (20%), 80 (12%), 67 [100% M-$(CH_2)_3$].

Method II

Heat under reflux 7.39 g (66.1 mmol) of cis-octahydrocyclopenta[b]pyrrole and 86 g (264.4 mmol) of mercuric acetate in 125 ml. of water for six days and extract as described in Method I to obtain approximately 3.4 g of the crude title compound of Part 1 as a light amber oil.

Method III

Heat under reflux 10.5 g (32.5 mmol) of octahydrocyclopenta[b]-pyrrole 3,5-dinitrobenzoate and 41.5 g (130 mmol) of Hg(OAc)$_2$ in 300 ml of 10% aqueous acetic acid for seven days and extract as described in Method I to obtain approximately 5.9 g of the crude title compound of Part 1 as a light amber oil.

2. Cis,Endo- and Cis,Exo-2-Cyanooctahydrocyclopenta[b]pyrrole

Method I

Dissolve 1.03 g of the crude reaction product from part 1 in 10 ml of water and 2 ml of methanol. Cool to approximately 0° C. and add 2 g of KCN. With stirring, add 2NHCl periodically over 3 hours to pH 6. Remove the cooling bath and stir overnight at ambient temperature. Warm to approximately 40° C. for one hour, cool to ambient temperature, remove the methanol in vacuo, oool to approximately 0°, basify with KOH to pH 11 and continuously extract with ether for 24 hours. Dry the ether extract over $K_2CO_3$, filter and remove the ether to obtain 0.84 g of a light amber oil which is a crude mixture of the two title compounds of Part 2, readily identified by gas liquid chromatographic (glc) analysis as a single peak for the binary mixture (instrument: Varian 3700; column length: 30 m; i.d.: 0.25 mm; film thickness: 0.25 $\mu$m; flame ionization detection temp: 300° C.; injector temp: 200° C.; injector mode: split; He flow rate: 0.5 ml/min); on Carbowax 20M, $R_t$ 6.34 min (column temp. 70° C. for 3 min., then increase 4° C./min) or $R_t$ 7.6 min. (column temp 60° C. for 3 min., then increase 2° C./min.), and on 100% biscyanopropylsilicone (SP 2340-Supelco Inc., Bellefonte, Pa.), $R_t$ 5.7 min (column temp. 120° C.) or 4.6 min (column temp. 150° C.). The two title compounds of Part 2 are also readily detected by TLC as individual components, $R_f$ 0.25 and 0.33 (0.25 mm silica, ether:hexanes-1:1).

Method II

To a stirred mixture of 1.5 g of the crude reaction product from Part 1, and 2 g of KCN in 15 ml of water at approximately 0° C., add 2N HCl periodically to pH 6. Remove the cooling bath and stir overnight at ambient temperature. Warm to 40° C. for one hour, cool to approximately 0° C., basify with KOH to pH 11 and extract as in Method I of Part 2 to obtain a crude mixture of the two title compounds as a light amber oil.

Isolation

Isolate the two epimeric products of Part 2 by any of the following methods:

(a) Isolate a binary mixture of the two epimeric products from Method I or II, Part 2 by preparative glc on an OV-17 column [⅛"×6'; 140° C.; He pressure 20 lbs.; $R_t$ 3.25 min ($R_t$ octahydrocyclopenta[b]pyrrole - 2.50 min)].

Similarly, Carbowax 20M or 100% biscyanopropylsilicone columns can be employed. If desired, separate the individual isomers by chromatography on silica gel.

(b) Dissolve 1.5 g of the crude products from Methods I or II, Part 2 in 23 ml of dry methylene chloride. Add 2.5 ml of pyridine, cool to approximately 0° C. and add dropwise 3.5 ml of trifluoroacetic anhydride. Allow the mixture to warm to ambient temperature overnight. Quench the reaction by slowly adding approximately 10 ml of 6N HCl. Remove the volatiles in vacuo and partition the residue between ether and 1N HCl. Wash the combined ether layers to neutrality with saturated sodium bicarbonate, dry over $MgSO_4$, filter and remove the ether in vacuo. Distill the residue in a kugelrohr oven (bulb to bulb, 70°-120° C./2.5 mm-0.3 mm) to obtain a mixture of the cis,endo- and cis,exo-2-cyano-1-trifluoroacetyloctahydrocyclopenta[b]pyrroles which is separated from the 1-trifluoroacetyl-cis-octahydrocyclopenta[b]pyrrole and other products by preparative thin layer chromatography (i.e., TLC - 200×200×1 mm silica; elute with ether:hexanes (2:3); two developments), column chromatography (silica gel), or by preparative glc on an OV-17 column (⅛"×6'; 210° C.); He pressure 20 lbs.; $R_t$ (isomeric mixture) 6.4 min.

If desired, separate the cis,endo and cis,exo-1-trifluoroacetyl-octahydrocyclopenta[b]pyrroles from each other by preparative TLC [200×200×1 mm] silica eluted with ether:hexanes (2:3); two developments) or by column chromatography (silica gel).

Cis,endo-2-cyano-1-trifluoroacetyloctahydrocyclopenta[b]pyrrole:

TLC: $R_f$ 0.5 (0.25 mm silica; ether:hexanes - 1:1);

GLC (see Method I of Part 2 for additional details):
Carbowax 20M-$R_t$ 10.3 min (column temp. 200° C. for 3 min then raise 10° C./min);

100% Biscyanopropylsilicone - $R_t$ 7.4 min (column temp. 245° C.).

MS: 232 (M+; 13%), 205 (M—HCN; 2%), 204 (M—H,HCN; 9%); 203 (M—$H_2$, HCN; 69%); 190 (M—$(CH_2)_3$; 11%); 179 (M—$CH_2$=CHCN; 11%); 163 (M—$CF_3$; 10%); 135 (M—$COCF_3$; 8%); 43 (100%)

NMR (200 MHz—$CDCl_3$): δ 4.95 (1H, doublet of doublets J=9 Hz, 4 Hz); 4.61 (1H, multiplet)

Cis,exo-2-cyano-1-trifluoroacetyl-octahydrocyclopenta[b]pyrrole:

TLC: $R_f$ 0.4 (0.25 mm silica; ether:hexanes (1:1));

GLC: (see Method 1 of Part 2 for further details):
Carbowax 20M - $R_t$ 10.7 min (column temp. 200° C. for 3 min then raise 10° C./min);

100% Biscyanopropylsilicone - $R_t$ 7.8 min (column temp. 245° C.).

MS: 232 (M+; 19%); 205 (M—HCN; 4%); 204 (M—H,HCN; 6%); 203 (M—$H_2$, HCN; 100%); 190 (M—$(CH_2)_3$; 7%); 179 (M—$CH_2$=CHCN; 6%); 163 (M—$CF_3$; 14%)

NMR: (200 MHz—$CDCl_3$): δ 4.94 (1H, triplet J=8 Hz); 4.54 (1H, multiplet)

Hydrolyze a mixture of cis,endo and cis,exo-2-cyano-1-trifluoroacetyloctahydrocyclopenta[b]pyrrole as obtained above, or hydrolyze the individual epimers as obtained above. For example, dissolve 2.5 g of cis,endo isomer in 20 ml of methanol containing approximately 2 g of $K_2CO_3$. Stir for seven hours, filter through celite, wash with ether and remove the solvents in vacuo. Partition the residue between $CH_2Cl_2$ and aqueous $K_2CO_3$ and wash the organic layer with additional aqueous $K_2CO_3$. Dry over $K_2CO_3$, filter, and remove the solvent in vacuo to obtain a mixture of 1.77 g of the cis,endo- (major component) and cis,exo-(minor component)2-cyano-octahydrocyclopenta[b]pyrrole epimers as an oil.

MS: 136 (M+; 29%); 135 (5%); 110 (M—CN; 100%); 109 (M-HCN; 24%); 108 (M—H,HCN; 17%); 107 (M—$H_2$, HCN; 46%); 93 (M—$H(CH_2)_3$; 20%); 82 (M—$CH_2$=CHCN; 43%); 81 (M—H,$CH_2$=CHCN; 22%); 80 (M—$H_2$,$CH_2$=CHCN; 19%); 68 (M—CN,$(CH_2)_3$; 24%); 67 (M—HCN,$(CH_2)_3$; 88%); 54 (M—$C_5H_9N$; 35%)

NMR (200 $MH_2$—$CDCl_3$): δ 5.05 (1H, broad) 4.55 (1H, multiplet) 4.13 (1H, multiplet) 2.81 (1H, multiplet) 2.62 (1H, multiplet) 2.27 (1H, multiplet)

3. Cis,Endo- and Cis,Exo-Octahydrocyclopenta[b]pyrrole-2-Carboxylic Acid Hydrochloride Reflux a solution of 0.85 g (6.2 mmol) of a mixture of cis,endo- and cis,exo-2-cyano octahydrocyclopenta[b]pyrrole (from Method I or II of Part 2) in 10 ml of 6N HCl for eight hours. Cool the reaction mixture to ambient temperature, remove the solvent under high vacuum and obtain the two title oompounds of Part 3 as a mixture, which appears as a single spot on TLC, $R_f$ 0.12 (0.25 mm silica; $CHCl_3$:isopropanol:7% $NH_4OH$ - 1:1:1 -lower phase).

4. Ethyl Cis,endo- and Ethyl Cis,Exo-Octahydrocyclopenta[b]pyrrole-2-Carboxylate a. Preparation of Hydrochloride salts

Dissolve the crude carboxylic acid hydrochloride obtained in Part 3 in 20 ml of absolute ethanol and 3 ml of triethyl orthoformate. Cool to approximately 0° C., bubble in HCl gas for 5 minutes and then reflux overnight CaSO$_4$ drying tube). Cool the reaction mixture to ambient temperature and remove the volatiles in vacuo. Suspend the resultant residue in 50 ml. of boiling THF, filter through celite, and remove the solvent in vacuo to obtain approximately 0.86 g of a mixture of the hydrochlorides of the two title compounds of Part 4, as a light tan solid. TLC (0.25 mm silica; 94.5% CH$_2$Cl$_2$:5% MeOH:0.5% NH$_4$OH, developed 3 times):

R$_f$- cis,endo-isomer: 0.60
R$_f$- cis,exo-isomer: 0.67 b. Separation of Epimers

Chromatograph the mixture of the ester hydrochlorides of Part 4a on silica gel (elute with ether:NH$_4$OH - 99:1)). Ethyl cis,exo-octahydrocyclopenta[b]pyrrole-2-carboxylate elutes first [MS: 183 (M+); 110 (M—CO$_2$CH$_2$CH$_3$, 100%); NMR (200 MHz—CDCl$_3$): δ 3.89 (1H br. triplet, J=5.6 Hz), δ 3.81 (1H triplet, J=6.4 Hz)], followed by ethyl cis,endo-octahydrocyclopenta[b]pyrrole- 2-carboxylate [MS: 183 (M+), 110 (M—CO$_2$CH$_2$CH$_3$, 100%); NMR (200 MHz-CDCl$_3$): δ 3.68 (1H br. multiplet), 3.62 (1H doublet of doublets, J=10 Hz, 6 Hz)].

The two epimeric products of this example are also readily assayed by glc on 100% biscyanopropylsilicone (170° C.), R$_t$ cis,exo isomer 6.2 min, R$_t$ cis,endo isomer 6.7 min (see Method I, Part 2 for additional details).

c. Preparation of Ethyl Cis,Endo-Octahydrocyclopenta[b]pyrrole-2-Carboxylate Hydrochloride Dissolve in ether the ethyl cis,endo-free base obtained in Part 4b and add 2.86 N ethereal HCl dropwise until precipitation is complete. Filter and recrystallize from CH$_2$Cl$_2$/CCl$_4$ or ethanol/ether to obtain the hydrochloride of the cis,endo-epimer of the product of Example 1, m.p. 170°–171° C.

NMR (400 MHz-d$_6$DMSO): δ 4.37 (1H, doublet of doublets J=11 Hz, 7 Hz); 4.22 (2H, doubled quartet J=7 Hz, 2 Hz); 4.00 (1H broad triplet J=7 Hz); 3.38 (2H singlet); 2.89 (1H multiplet); 2.43 (1H multiplet); 1.99 (1H multiplet); 1.85-1.53 (5H multiplet); 1.49 (1H multiplet); 1.24 (3H triplet J=7 Hz).

d. Preparation of Ethyl Cis,Exo-Octahydrocyclopenta[b]pyrrole-2-Carboxylate Hydrochloride Treat the cis,exo-free base obtained in Part 4b in a manner identical to that described in Part 4c to obtain the hydrochloride of the cis,exo-epimer of the product of Example 1, m.p. 111.5°–113.5° C.

NMR (400 MHz - d$_6$DMSO): δ4.49 (1H, triplet J=8 Hz); 4.24 (2H, quartet J=7 Hz); 4.13 (1H doublet of doublets J=7 Hz, 1.5 Hz); 3.34 (2H singlet); 2.77 (1H multiplet); 2.21 (1H multiplet); 1.99 (1H multiplet); 1.87 (2H multiplet); 1.75 (2H multiplet); 1.50 (2H multiplet); 1.25 (3H triplet J=7 Hz).

EXAMPLE 2

Ethyl Cis,Endo-Octahydrocyclopenta[b]Pyrrole-2-Carboxylate

Method I

See Example 1, B(4)(b) (free base) and Example 1, B(4)(c) (hydrochloride).

Method II

A. Ethyl 1-Benzyl-1,4,5,6-Tetrahydrocyclopenta[b]Pyrrole-2-Carboxylate

Add dropwise 3.9 gm of ethyl bromopyruvate in 50 ml of ethanol to a flask containing 3.46 gm of benzyliminocyclopentane and 2.0 g of triethylamine in 50 ml of ethanol at 0° C., stir for 2 hours, then heat to reflux for 2 hours. Concentrate the reaction mixture and partition between 1N HCl and ether. Dry the ether extract over magnesium sulfate, filter, ooncentrate under high vacuum to obtain a brown oil and distill in a kugelrohr at 190°–210°/0.1 mm to obtain the title compound of Part A as a yellow oil.

B. Ethyl Cis,Endo-octahydrocyclopenta[b]pyrrole-2-Carboxylate Hydrochloride Introduce hydrogen gas to a mixture of 2.3 gm of the pyrrole compound produced in Method II, part A of this Example and 1.5 gm of 20% Pd(OH)$_2$/C in 200 ml of ethanol, and stir the reaction mixture. After 24 hours add an additional 0.8 gm of the palladium catalyst. After 600 ml of hydrogen gas is absorbed, filter the reaction mixture and concentrate to obtain a liquid and a solid. Take up the liquid in ether and filter. Treat the filtrate with 2.86N HCl/ether to obtain an oil which solidifies. Filter off the solid to obtain the hydrochloride salt of the title compound of Part B as a beige solid, m.p. 163°–7° C. Recrystallization from CH$_2$Cl$_2$ and hexane raises the melting point to 171°–2° C.

C. Cis,Endo-Octahydrocyclopenta[b]pyrrole-2-Carboxylic Acid

Stir a mixture of 10.7 g of ethyl cis,endo-octahydrocyclopenta[b]pyrrole-2-carboxylate hydrochloride (from Part B above) and 175 ml of 1N sodium hydroxide at room temperature for 20 hours and then concentrate in vacuo. Place the residue on a silica gel (1000 g, 60–200 mesh) column and elute with chloroform:isopropanol:7% ammonium hydroxide 1:1:1 (organic layer) to give cis,endo-octahydrocyclopenta[b]pyrrole-2-carboxylic acid, as a white solid, m.p. 220°–222° C.; TLC: R$_f$ 0.12 (0.25 mm silica; CHCl$_3$:isopropanol:7% NH$_4$OH–1:1:1–lower phase); MS: 156, 155 (M+), 126 (M—HCO), 111 (M—CO$_2$), 110 (M—CO$_2$H; 100%), 93 [M—H(CH$_2$)$_3$], 82 (M—CH$_2$=CHCO$_2$H), 80 (M—H$_2$,CH$_2$=CHCO$_2$H), 68 [M—CO$_2$H, (CH$_2$)$_3$], 67 [M—HCO$_2$H,(CH$_2$)$_3$].

NMR (400 MHz-D$_2$O); δ4.39 (1H doublet of doublets J=11 Hz,8 Hz); 4.20 (1H multiplet); 3.00 (1H multiplet); 2.66 (1H multiplet); 2.03-1.78 (6H multiplet); 1.57 (1H multiplet).

Method III

Dissolve 0.058 g of ethyl cis,exo-octahydrocyclopenta[b]pyrrole-2-carboxylate (from Example 1, B(4)(b) or from Example 5) in 20 ml of ethanol and 2 ml of triethylamine. Reflux under nitrogen for two days to obtain an equilibrium mixture consisting of approximately 25% of the cis,endo epimeric product of this method and 75% of the cis,exo epimeric starting material of this method. Remove the volatiles in vacuo and isolate the product of this Example as in Example 1, B(4)(b). To obtain the hydrochloride salt of the product of this example, treat the free base with etheral HCl as exemplified in Method II, Part B above, and in Example 1, B(4)(c).

Method IV

Dissolve 0.5 g of ethyl cis,exo-octahydrocyclopenta[b]pyrrole-22-carboxylate in 20 ml of absolute ethanol contain 0.66 g of potassium t-butoxide. Reflux under nitrogen for 18 hours, cool to ambient temperature and quench with solid NH4Cl. Remove the solvent in vacuo, suspend the residue in 50 ml of boiling THF, filter through celite, remove the THF in vacuo and separate the product of this example from its cis,exo epimer as in Example 1, B(4)(b). The hydrochloride salt of the product of this Example may be obtained as in Method III.

Method V

Allow 0.5 g of ethyl cis,exo-octahydrocyclopenta[b]pyrrole-2-carboxylate in 20 ml of absolute ethanol to stand at room temperature for one to two weeks. Remove the ethanol in vacuo and isolate the product of this example as in Example 1, B(4)(b). The hydrochloride salt of the product may be obtained as in Method III.

The product of Example 2 is used in part A of Example 3 as the intermediate for producing the title compound of Example 3.

EXAMPLE 3

1-[N-(1(R,S)-Carboethoxy-3-Phenylpropyl)-(S)-Alanyl]-Cis,Endo-Octahydrocyclopenta[b]Pyrrole-2(S)-Carboxylic Acid A. To a solution of 10.0 g of ethyl-cis,endo-octahydrocyclopenta[b]pyrrole-2-carboxylate in 400 ml of ethyl acetate add 17.0 g of N-benzyloxycarbonyl-(S)-alanine, N-hydroxysuccinimide ester. Stir the reaction mixture at room temperature for 20 hours and concentrate it in vacuo. Place the residue on a column of silica gel (3000 g, 60–200 mesh) and elute with chloroform:ethyl acetate 10:1 to obtain 1-[N-benzyloxycarbonyl-(S)-alanyl]-cis,endo-octahydrocyclopenta[b]pyrrole-2-carboxylic acid, ethyl ester, a colorless oil $[\alpha]_D^{26}$-32.6° (C=0.5, ethanol).

B. To a solution of 3.22 g of 1-[N-benzyloxycarbonyl-(S)-alanyl]-cis,endo-octahydrocyclopenta[b]pyrrole-2-carboxylic acid, ethyl ester in 150 ml of methanol, add 20 ml of 2.5N sodium hdroxide and stir the mixture at room temperature for 18 hours. Concentrate the mixture under nitrogen, dilute the residue with ice-water and then make the mixture acidic with concentrated hydrochloric acid. Extract the aqueous solution with ethyl acetate and dry the organic phase over magnesium sulfate. Concentrate the organic phase and place it on a column of silica gel (500 g., 60–200 mesh). Elute with chloroform:glacial acetic acid 9:1 and isolate 1-[N-benzyloxycarbonyl-(S)-alanyl]-cis,endo-octahydrocyclopenta[b]pyrrole-2(S)-carboxylic acid, as a colorless oil, $[\alpha]_D^{26}$-26.4° (C=0.5, ethanol).

C. Dissolve 1.70 g of 1-[N-benzyloxycarbonyl-(S)-alanyl]-cis,endo-octahydrocyclopenta[b]pyrrole-2(S)-carboxylic acid in 100 ml of methanol. Add 0.40 g 10% palladium-on-charcoal and hydrogenate the mixture at atmospheric pressure. Filter the mixture and concentrate in vacuo to obtain 1-[(S)-alanyl]-cis,endo-octahydrocyclopenta[b]pyrrole-2(S)-carboxylic acid.

D. Dissolve 1-[(S)-alanyl]-cis,endo-octahydrocyclopenta[b]pyrrole-2(S)-carboxylic acid in 100 ml of absolute methanol. Add 1.10 g 2-oxo-4-phenylbutyric acid, ethyl ester and 20 ml of 3 Angstrom molecular sieve pellets, and stir the resulting mixture at room temperature for eighteen hours. Filter the reaction mixture and treat the filtrate with 0.68 g sodium cyanoborohydride at room temperature for two hours. Concentrate the mixture under nitrogen and dilute the oil with dilute hydrochloric acid and stir at room temperature for one hour. Absorb the aqueous solution on 200 ml of a XAD-2 (Rohm & Haas Co. resin). Elute the resin with 2000 ml of water and then with 2000 ml of methanol. Concentrate the methanol solution and place the residue on a column of silica gel (400 g, 60–200 mesh) and elute with chloroform:isopropanol:7% ammonium hydroxide (1:1:1) (organic layer) to give 1-[N-(1(R,S)-carboethoxy-3-phenylpropyl)-(S)-alanyl]-cis,endo-octahydrocyclopenta[b]pyrrole-2(S)-carboxylic acid, as a colorless oil, $[\alpha]_D^{26}$-5.8° (C=10.6, ethanol).

EXAMPLE 4

1-[N-(1(S)-Carboethoxy-3-Phenylpropyl-(S)-Alanyl]-Cis,Endo-Octahydrocyclopenta[b]Pyrrole-2(S)-Carboxylic Acid and the Hydrochloride Salt Thereof

Method I

A. Cis,endo-Octahydrocyclopenta[b]pyrrole-2-Carboxylic Acid Hydrochloride

Method I

Add a 20% HCl in dioxane solution (100 ml) to 5 g. of cis,endo-octahydrocyclopenta[b]pyrrole-2-carboxylic acid. Stir the resulting mixture at room temperature for 30 min. and then concentrate it in vacuo. Wash the white residue with anhydrous ether and dry in vacuo to obtain the title compound of Part A as a white solid, m.p. 209°–211°.

Method II

Dissolve 0.2 g of ethyl cis,endo-octahydrocyclopenta[b]pyrrole-2-carboxylate (free base or hydrochloride from Example 2 in 20 ml of 6N hydrochloric acid and reflux overnight. Cool the reaction mixture, remove the volatiles under high vacuum and obtain the title product of Part A.

B. To 5.0 g of the product of Part A, add 50 ml of benzyl alcohol and 50 ml of thionyl chloride and stir at room temperature. Concentrate the reaction mixture in vacuo and recrystallize the residue from chloroform/isopropanol to give benzyl cis,endo-octahydrocyclopenta[b]pyrrole-2-carboxylate hydrochloride, m.p. 175°.

C. To 5.5 g of the product of Part B, add 2.6 g of 1-hydroxybenzotriazole, 5.4 g of N[1(S)-carboethoxy-3-phenylpropyl]-(S)-alanine and 4.0 g of dicyclohexylcarbodiimide in 80 ml of dimethyl formamide. Stir the reaction mixture at room temperature for 18 hours. Filter the reaction mixture, and add ethyl acetate to the filtrate. Extract the ethyl acetate solution (3×200 ml) with 5% aqueous sodium bicarbonate. Concentrate the dried (MgSO₄) ethyl acetate solution in vacuo. Chromatograph the residue on a silica gel column (400 g, 60-200 mesh) and elute with ethyl acetate/petroleum ether (30°-60°) 2:1. Isolate, as the first eluted material, 1-[N-(1(S)-carboethoxy-3-phenylpropyl)-(S)-alanyl]-cis,endo-octahydrocyclopenta[b]pyrrole-2(S)-carboxylic acid benzyl ester.

D. Hydrogenate 3.0 g of 1-[N-(1(S)-carboethoxy-3-phenylpropyl)-(S)-alanyl]-cis,endo-octahydrocyclopenta[b]pyrrole-2(S)-carboxylic acid benzyl ester in 40 ml of ethanol containing 0.5 g of 10% Pd/C. Remove the catalyst by filtration and concentrate the filtrate in vacuo. Add absolute ether to crystallize 1-[N-(1(S)-carboethoxy-3-phenylpropyl)-(S)-alanyl]-cis,endo-octahydrocyclopenta[b]pyrrole-2(S)-carboxylic acid, m.p. 110°-112° C.(d).

E. Add dropwise, with stirring, a solution of 1.3M hydrochloric acid in ether to the product of Part D until the mixture is pH2. Add 100 ml of ether and continue to stir for 30 minutes, then filter to obtain 1-[N-1(S)-carboethoxy-3-phenylpropyl)-(S)-alanyl]-cis,endo-octahydrocyclopenta[b]pyrrole-2(S)-carboxylic acid hydrochloride.

Method II

A. Stir a solution of 4.56 g of N-[1(S)-carboethoxy-3-phenylpropyl]-(S)-alanine, 2.20 g of N-hydroxysuccinimide and 3.80 g of 1-(3-dimethylaminopropyl)-3-ethylcarbodiimide hydrochloride in 30 ml of dimethylformamide for 18 hours at room temperature. Dilute the reaction mixture with ethyl acetate and wash the ethyl acetate layer with saturated aqueous sodium chloride. Concentrate the dried (MgSO₄) ethyl acetate solution to give N-[1(S)-carboethoxy-3-phenylpropyl]-(S)-alanine N-hydroxysuccinimide ester.

B. To a mixture of 3.76 g of the product of Part A and 1.55 g of cis,endo-octahydrocyclopenta[b]pyrrole-2-carboxylic acid in 30 ml of dimethylformamide, add 1.5 ml of triethylamine and stir the resulting mixture at room temperature for 18 hours. Concentrate the reaction mixture in vacuo and partition between ethyl acetate and H₂O (adjusted to pH 4). Wash the ethyl acetate solution with saturated aqueous sodium chloride. Concentrate the dried (MgSO₄) ethyl acetate solution in vacuo and chromatograph the residue on a silica gel (1000 ml) column using CHCl₃/iso-PrOH/7% NH₄OH-1:1:1 (organic phase). Isolate 1-[N-(1(S)-carboethoxy-3-phenylpropyl)-(S)-alanyl]-cis,endo-octahydrocyclopenta[b]pyrrole-2(S)-carboxylic acid as a foam.

EXAMPLE 5

Ethyl Cis,Exo-Octahydrocyclopenta[b]Pyrrole-2-Carboxylate

Method I

See Example 1, B(4)(b) (free base) and Example 1, B(4)(d) (hydrochloride salt).

Method II

Dissolve 0.4 g of ethyl cis,endo-octahydrocyclopenta[b]pyrrole-2-carboxylate (as prepared in Example 1, B(4)(b) or Example 2) in 40 ml of ethanol and 7 ml of triethylamine. Reflux under nitrogen for five days. Remove the volatiles in vacuo and isolate the product of this example as in Example 1, B(4)(b). To obtain the hydrochloride salt of the product of this example, treat the free base with ethereal HCl as exemplified in Example 1 B(4)(d).

Method III

Substituting 0.5 g of ethyl cis,endo-octahydrocyclopenta[b]pyrrole-2-carboxylate for the cis,exo epimer, follow the procedure described in Method IV of Example 2 to obtain the product of this example. The hydrochloride salt may be obtained as in Method II.

Method IV

Substituting 0.5 g of ethyl cis,endo-octahydrocyclopenta[b]pyrrole-2-carboxylate for the cis,exo epimer, follow the procedure described in Method V of Example 2 to obtain the product of this example. The hydrochloride salt may be obtained as in Method II.

EXAMPLE 6

Cis,Exo-Octahydrocyclopenta[b]Pyrrole-2-Carboxylic Acid

Substituting ethyl cis,exo-octahydrocyclopenta[b]pyrrole-2-carboxylate (from Example 5 or from Example 1, B(4)(d) for the cis,endo-epimer, follow the hydrolysis procedure of Example 2C, Method II to obtain the product of this example. TLC: R$_f$0.12 (0.25 mm silica; CHCl₃:isopropanol:7% NH₄OH-1:1:1-lower phase).

EXAMPLE 7

Cis,Exo-Octahydrocyclopenta[b]Pyrrole-2-Carboxylic Acid Hydrochloride

Method I

Substituting the cis,exo-acid product of Example 6 for the cis,endo-epimer, follow the procedure of Example 4A, Method I to obtain the product of this example.

NMR (400 MHz-D₂O): δ4.50 (1H triplet J=5 Hz); 4.29 (1H doubled triplet J=9 Hz, 3.5 Hz); 2.96 (1H multiplet); 2.38 (1H multiplet); 2.14 (1H multiplet); 2.05 (1H multiplet); 1.88 (1H multiplet); 1.80-1.60 (3H multiplet); 1.53 (1H multiplet).

Method II

Dissolve 0.2 g of ethyl cis,exo-octahydrocyclopenta[b]pyrrole-2-carboxylate [free base or hydrochloride from Example 5 or Example 1, B(4)(b) or (d)] in 20 ml of 6N hydrochloric acid and reflux overnight. Cool the reaction mixture and remove the volatiles under high vacuum to obtain the product of this example. MS (FAB): 311 (2M+H; 5%), 156 (M+H; 100%), 112 (M+H—CO₂; 12%), 110 (M—CO₂H; 42%).

EXAMPLE 8

Benzyl Cis,Exo-Octahydrocyclopenta[b]Pyrrole-2-Carboxylate

To 5.0 g of the product of Example 7, add 50 ml of benzyl alcohol and 50 ml of thionyl chloride and stir at room temperature. Concentrate the reaction mixture in vacuo and recrystallize the residue from chloroform/isopropanol to give benzyl cis,exo-octahydrocyclopenta-[b]pyrrole-2-carboxylate hydrochloride.

EXAMPLE 9

1-[N-(1(S)-Carboethoxy-3-Phenylpropyl)-(S)-Alanyl]-Cis,Exo-Octahydrocyclopenta[b]Pyrrole-2(S)-Carboxylic Acid and the Hydrochloride Salt Thereof

Method I

Substituting the product of Example 8 for the cis,endo-epimer, follow the procedures of Example 4, Parts C, D and E of Method I to obtain the product of this example, as the free amino acid or as its hydrochloride salt.

Method II

Substituting the product of Example 6 for the cis,endo-epimer, follow the procedures in Method II of Example 4 to obtain the product of this example.

EXAMPLE 10

1-[N-(1(S)-Carboxy-3-Phenylpropyl)-(S)-Alanyl]-Cis, Endo-Octahydrocyclopenta[b]Pyrrole-2(S)-Carboxylic Acid and the Hydrochloride Salt Thereof A. To a solution of 0.80 g of 1[N-(1(S)-carboethoxy-3-phenylpropyl)-(S)-alanyl]-cis,endo-octahydrocyclopenta[b]pyrrole-2(S)-carboxylic acid from Example 4 in 100 ml of methanol at 0°–5° C., add 2.0 ml of 2.5N sodium hydroxide solution and stir at room temperature for 24 hours. Concentrate this solution in vacuo and absorb on 350 ml of AG50W-X2 Bio-Rad resin (100-200 mesh, hydrogen form). Wash the column with water until the eluate is neutral and elute the product with pyridine:H$_2$O (1:24). Concentrate the uluate in vacuo and chromatograph on a Lobar RP-8, size B column (E. Merck) using acetonitrile:water (2:3) as eluant to obtain the title compound of this example as the free amino acid.

B. Treat an ethanol solution of the product of Part A with one equivalent of a 1N solution of ethanolic hydrogen chloride. Remove the solvent in vacuo at room temperature to obtain the hydrochloride salt of the title compound of this example.

Similarly, prepare the following compounds:

1[Nα-(1(S)-carboethoxy-3-phenylpropyl)-(S)-lysyl]-cis,endo-octahydrocyclopenta[b]pyrrole-2(S)-carboxylic acid.
1[Nα-(1(S)-carboethoxy-3-phenylpropyl)-(S)-lysyl]-cis,endo-octahydrocyclopenta[b]pyrrole-2(S)-carboxylic acid hydrochloride.
1[Nα-(1(S)-carboethoxy-3-phenylpropyl)-(S)-lysyl]-cis,endo-octahydrocyclopenta[b]pyrrole-2(S)-carboxylic acid dihydrochloride.
1-[Nα-(1(S)-carboxy-3-phenylpropyl)-(S)-lysyl]-cis,endo-octahydrocyclopenta[b]pyrrole-2(S)-carboxylic acid.
1-[Nα-(1(S)-carboxy-3-phenylpropyl)-(S)-lysyl]-cis,endo-octahydrocyclopenta[b]pyrrole-2(S)-carboxylic acid hydrochloride.
1-p8 Nα-(1(S)-carboxy-3-phenylpropyl-(S)-lysyl]-cis,endo-octahydrocyclopenta[b]pyrrole-2(S)-carboxylic acid dihydrochloride.
1-[N-(1(S)-carboethoxybutyl)-(S)-alanyl]-cis,endo-octahydrocyclopenta[b]pyrrole-2(S)-carboxylic acid.
1-[N-(1(S)-carboethoxybutyl)-(S)-alanyl]-cis,endo-octahydrocyclopenta[b]pyrrole-2(S)-carboxylic acid hydrochloride.
1-[N-(1(S)-carboxybutyl)-(S)-alanyl]-cis,endo-octahydrocyclopenta[b]pyrrole-2(S)-carboxylic acid.
1-[N-(1(S)-carboxybutyl)-(S)-alanyl]-cis,endo-octahydrocyclopenta[b]pyrrole-2(S)-carboxylic acid hydrochloride.
1-[Nα-(1(S)-carboethoxybutyl)-(S)-lysyl]-cis,endo-octahydrocyclopenta[b]pyrrole-2(S)-carboxylic acid.
1-[Nα-(1(S)-carboethoxybutyl-(S)-lysyl]-cis,endo-octahydrocyclopenta[b]pyrrole-2(S)-carboxylic acid hydrochloride.
1-[Nα-(1(S)-carboethoxybutyl)-(S)-lysyl]-cis,endo-octahydrocyclopenta[b]pyrrole-2(S)-carboxylic acid dihydrochloride.
1-[Nα-(1(S)-carboxybutyl)-(S)-lysyl]-cis,endo-octahydrocyclopenta[b]pyrrole-2(S)-carboxylic acid.
1-[Nα-(1(S)-carboxybutyl)-(S)-lysyl]-cis,endo-octahydrocyclopenta[b]pyrrole-2(S)-carboxylic acid hydrochloride.
1-[Nα-(1(S)-carboxybutyl)-(S)-lysyl]-cis,endo-octahydrocyclopenta[b]pyrrole-2(S)-carboxylic acid dihydrochloride.
1-[N-(1(S)-carboxy-3-phenylpropyl)-(S)-alanyl]-cis,exo-octahydrocyclopenta[b]pyrrole-2(S)-carboxylic acid.
1-[N-(1(S)-carboxy-3-phenylpropyl)-(S)-alanyl]-cis,exo-octahydrocyclopenta[b]pyrrole-2(S)-carboxylic acid hydrochloride.
1[Nα-(1(S)-carboethoxy-3-phenylpropyl)-(S)-lysyl]-cis,exo-octahydrocyclopenta[b]pyrrole-2(S)-carboxylic acid.
1[Nα-(1(S)-carboethoxy-3-phenylpropyl)-(S)-lysyl]-cis,exo-octahydrocyclopenta[b]pyrrole-2(S)-carboxylic acid hydrochloride.
1[Nα-(1(S)-carboethoxy-3-phenylpropyl)-(S)-lysyl]-cis,exo-octahydrocyclopenta[b]pyrrole-2(S)-carboxylic acid dihydrochloride.
1-[Nα-(1(S)-carboxy-3-phenylpropyl)-(S)-lysyl]-cis,exo-octahydrocyclopenta[b]pyrrole-2(S)-carboxylic acid.
1-[Nα-(1(S)-carboxy-3-phenylpropyl)-(S)-lysyl]-cis,exo-octahydrocyclopenta[b]pyrrole-2(S)-carboxylic acid hydrochloride.
1-[Nα-(1(S)-carboxy-3-phenylpropyl)-(S)-lysyl]-cis,exo-octahydrocyclopenta[b]pyrrole-2(S)-carboxylic acid dihydrochloride.
1-[N-(1(S)-carboethoxybutyl)-(S)-alanyl]-cis,exo-octahydrocyclopenta[b]pyrrole-2(S)-carboxylic acid.
1-[N-(1(S)-carboethoxybutyl)-(S)-alanyl]-cis,exo-octahydrocyclopenta[b]pyrrole-2(S)-carboxylic acid hydrochloride.
1-[N-(1(S)-carboxybutyl)-(S)-alanyl]-cis,exo-octahydrocyclopenta[b]pyrrole-2(S)-carboxylic acid.
1-[N-(1(S)-carboxybutyl)-(S)-alanyl]-cis,exo-octahydrocyclopenta[b]pyrrole-2(S)-carboxylic acid hydrochloride.
1-[Nα-(1(S)-carboethoxybutyl)-(S)-lysyl]-cis,exo-octahydrocyclopenta[b]pyrrole-2(S)-carboxylic acid.
1-[Nα-(1(S)-carboethoxybutyl)-(S)-lysyl]-cis,exo-octahydrocyclopenta[b]pyrrole-2(S)-carboxylic acid hydrochloride.
1-[Nα-(1(S)-carboethoxybutyl)-(S)-lysyl]-cis,exo-octahydrocyclopenta[b]pyrrole-2(S)-carboxylic acid dihydrochloride.
1-[Nα-(1(S)-carboxybutyl)-(S)-lysyl]-cis,exo-octahydrocyclopenta[b]pyrrole-2(S)-carboxylic acid.
1-[Nα-(1(S)-carboxybutyl)-(S)-lysyl]-cis,exo-octahydrocyclopenta[b]pyrrole-2(S)-carboxylic acid hydrochloride.
1-[Nα-(1(S)-carboxybutyl)-(S)-lysyl]-cis,exo-octahydrocyclopenta[b]pyrrole-2(S)-carboxylic acid dihydrochloride.

The compounds of this invention are useful in view of their pharmacological properties. In particular, they possess activity as antihypertensive agents as evidenced by their ability to reduce blood pressure in mammals, including humans, in which the blood pressure has become abnormally elevated.

The compounds of the present invention can be combined with pharmaceutical carriers and administered in a variety of well known pharmaceutical forms suitable for oral or parenteral administration to provide compositions useful in the treatment of cardiovascular disorders and particularly mammalian hypertension.

The effective dose ($ED_{50}$) of the compounds of this invention will typically be in the range of about 0.01 to about 30 mg/kg, preferably about 0.1 to about 10 mg/kg, of mammalian weight, administered in single or divided doses. The exact dose to be administered is determined by the attending clinician and is dependent upon where the particular compound lies within the above quoted range, as well as upon the age, weight and condition of the individual.

Generally, in treating humans, the compounds of this invention may be administered to patients in need of such treatment in a dosage range of 5 to 500 mg per patient generally given several times, thus giving a total daily dose of from 5 to 2000 mg per day. Also, the compounds of this invention may be given in combination with diuretics or other antihypertensives. Typically, these are combinations whose individual per day dosages range from one-fifth of the minimally recommended clinical dosages to the maximum recommended levels for the entities when they are given singly. Examples of such diuretics or other antihypertensives are hydrochlorothiazide, chlorothiazide, ethacrynic acid, amiloride, furosemide, propanolol, timolol and methyldopa.

Since the compounds of the present invention are believed to act as angiotensin converting enzyme inhibitors, it is also contemplated that they may be used in treating other cardiovascular disorders, for example congestive heart failure, in the same manner as other ACE inhibitors such as captopril and enalapril may be used. In addition, the compounds of this invention may be used in the treatment of glaucoma by topical application.

The composition containing the compounds of this invention will preferably contain about 5 to about 250 mg of the active compound per dosage unit. These compositions are most preferably administered orally. Typical formulations for oral administration are those such as tablets, capsules, syrups, elixirs or suspensions. Typical injectable formulations include solutions and suspensions.

Typical acceptable pharmaceutical carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate, polyvinylpyrrolidone, polyvinyl alcohol; stearic acid; alkaline earth metal stearates such as magnesium stearate and calcium stearate, stearic acid vegetable oils such as peanut oil, cottonseed oil, sesame oil, olive oil and corn oil; non-ionic, cationic and anionic surfactants; ethylene glycol polymers; beta-cyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

For treatment of glaucoma, a compound of this invention is preferably administered in the form of ophthalmic pharmaceutical compositions adapted for topical administration to the eye, such as solutions, ointments or solid inserts. Formulations of these compounds may contain from 0.01 to 5% and especially 0.25 to 2% of medicament. Other concentrations may be employed provided the dose is effective in lowering intraocular pressure. As a unit dosage form, between 0.01 to 2.5 mg., preferably 0.05 to 2.5 mg., and especially 0.1 to 1.0 mg. of the active compound is applied to the human eye, generally on a daily basis. Individual dosage requirements are variable, however, and must be administered on the basis of the severity of the disease and the response of the patient.

Typical pharmaceutical carriers for topical opthalmological administration are well known in the art, see for example U.S. Pat. No. 4,312,863, the relevant portions of which are herein incorporated by reference.

The following examples describe in detail compositions that are illustrative of the present invention. It will be apparent to those skilled in the art that many modifications, both of materials and methods, may be practiced without departing from the purpose and intent of this disclosure.

In the following examples, the active ingredient is 1-{[N-[1(S)-carboethoxy-3-phenylpropyl]-(S)-alanyl]}-cis,endo-octahydrocyclopenta[b]pyrrole-2(S)-carboxylic acid or equivalent amounts of its pharmaceutically acceptable salts.

EXAMPLE 11

| Capsule | Amount | (mg) |
|---|---|---|
| Active ingredient | 250.0 | 125.0 |
| Lactose | 173.0 | 86.5 |
| Corn Starch | 75.0 | 37.5 |
| Magnesium Stearate | 2.0 | 1.0 |
| | 500.0 | 250.0 |

Blend the active ingredient, lactose and corn starch until uniform; then blend the magnesium stearage into the resulting powder. Encapsulate the mixture into suitably sized two-piece hard gelatin capsules.

EXAMPLE 12

| Tablet | Amount | (mg) |
|---|---|---|
| Active ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| | 500.0 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

EXAMPLE 13

| Injectable Solution | mg/ml |
|---|---|
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad | 1.0 ml |

Dissolve the p-hydroxybenzoates in a portion of water for injection at 60°–70° C. and cool the solution to 25°–35° C. Charge and dissolve all other excipients and the active ingredient. Bring the solution to final volume, filter it through a sterilizing membrane and fill into sterile containers.

EXAMPLE 14

| Ophthalmic Solution | Amount (mg) |
|---|---|
| Active ingredient | 1 |
| Sodium phosphate monobasic 2H$_2$O | 9.38 |
| Dibasic sodium phosphase 12H$_2$O | 28.48 |
| Benzalkonium chloride | 0.10 |
| Sodium hydroxide q.s. | pH 6.8 |
| Water q.s. ad. | 1.0 ml |

The active ingredient, phosphate buffer salts and benzalkonium chloride are added to and dissolved in water. The pH of the solution is adjusted to 6.8 with sodium hydroxide and the final solution diluted to volume. The solution is rendered sterile by filtration through a sterilizing filter.

Following the procedures of Examples 11, 12, 13 and 14, substitute other compounds of the present invention for 1-{[N-[1(S)-carboethoxy-3-phenylpropyl]-(S)-alanyl}-cis,endo-octahydrocyclopenta[b]pyrrole-2(S)-carboxylic acid to prepare other compositions of the present invention.

We claim:
1. A process for the preparation of cis,endo-octahydrocyclopenta[b]pyrrole-2-carboxylates which comprises:
    (1) the reaction of a halo pyruvate ester with benzyliminocyclopentane in an inert solvent in the presence of a base at 0°–100° C. for about 2–8 hours; and
    (2) catalytically reducing the product of step 1 to form cis,endo-octahydrocyclopenta[b]-pyrrole-2-carboxylate.

* * * * *